(12) United States Patent
Dijksman et al.

(10) Patent No.: US 8,990,018 B2
(45) Date of Patent: Mar. 24, 2015

(54) METHOD OF PREPARING A SWALLOWABLE CAPSULE COMPRISING A SENSOR

(75) Inventors: Johan Frederik Dijksman, Eindhoven (NL); Anke Pierik, Eindhoven (NL); Judith Margreet Rensen, Eindhoven (NL); Jeff Shimizu, Cortlandt Manor, NY (US); Petrus Leonardus Adrianus Van Der Made, Eindhoven (NL); Michel Gerardus Pardoel, Eindhoven (NL); Frits Tobi De Jongh, Eindhoven (NL); Johan Gerard Kleibeuker, Eindhoven (NL)

(73) Assignee: Medimetrics Personalized Drug Delivery B.V., Eindhoven (NL)

( * ) Notice: Subject to any disclaimer, the term of this patent is extended or adjusted under 35 U.S.C. 154(b) by 1150 days.

(21) Appl. No.: 12/933,891

(22) PCT Filed: Mar. 24, 2009

(86) PCT No.: PCT/IB2009/051215
§ 371 (c)(1),
(2), (4) Date: Sep. 22, 2010

(87) PCT Pub. No.: WO2009/122323
PCT Pub. Date: Oct. 8, 2009

(65) Prior Publication Data
US 2011/0017612 A1    Jan. 27, 2011

(30) Foreign Application Priority Data

Mar. 31, 2008    (EP) .................................... 08153741

(51) Int. Cl.
*G06F 19/00*    (2011.01)
*A61B 5/04*    (2006.01)
(Continued)

(52) U.S. Cl.
CPC ............. *A61B 5/073* (2013.01); *A61B 5/14539* (2013.01); *A61B 5/1495* (2013.01); *A61B 2560/0223* (2013.01)
USPC ............................... 702/1; 600/373; 206/538

(58) Field of Classification Search
USPC ..................... 702/1, 19, 22, 25, 85, 104, 127, 702/182–183, 424; 424/9.1, 422–423, 451, 424/455; 600/345, 361, 372–373; 604/19, 604/27–28; 204/194, 403.01, 433; 206/528, 206/530–531, 535, 538–539
See application file for complete search history.

(56) References Cited

U.S. PATENT DOCUMENTS

| | | | |
|---|---|---|---|
| 3,791,377 A | 2/1974 | Norby et al. | |
| 4,572,403 A | 2/1986 | Benaroya | |

(Continued)

FOREIGN PATENT DOCUMENTS

| | | |
|---|---|---|
| CN | 1774239 | 5/2006 |
| CN | 1958090 | 5/2007 |

(Continued)

OTHER PUBLICATIONS

Kunz et al., A pH-Measuring Radio Capsule for the Alimentary Canal, Aug. 1971, Digestive Diseases, vol. 16, No. 8, pp. 739-743.*

(Continued)

*Primary Examiner* — Toan Le
(74) *Attorney, Agent, or Firm* — Lee & Hayes, PLLC

(57) ABSTRACT

A kit includes a swallowable capsule (1, 45) with a potentiometric sensor (3), such as a pH sensor, with an unfilled electrolyte cell (31). The kit further includes a separate container (46) containing a liquid electrolyte. The kit can, e.g., be packed in a blister package. After unpacking the capsule the electrolyte cell (31) is filled with the electrolyte.

10 Claims, 4 Drawing Sheets

(51) Int. Cl.
*B65D 83/04* (2006.01)
*A61B 5/07* (2006.01)
*A61B 5/145* (2006.01)
*A61B 5/1495* (2006.01)

(56) References Cited

U.S. PATENT DOCUMENTS

| | | | |
|---|---|---|---|
| 4,575,410 | A | 3/1986 | Neti |
| 4,814,180 | A | 3/1989 | Eckenhoff et al. |
| 5,279,607 | A | 1/1994 | Schentag et al. |
| 5,318,557 | A | 6/1994 | Gross |
| 5,567,592 | A | 10/1996 | Benet et al. |
| 6,803,373 | B2 | 10/2004 | Schellens |
| 7,030,132 | B2 | 4/2006 | Schellens et al. |
| 2003/0020810 | A1 | 1/2003 | Takizawa et al. |
| 2003/0213495 | A1 | 11/2003 | Fujita et al. |
| 2004/0106849 | A1 | 6/2004 | Cho et al. |
| 2004/0242962 | A1 | 12/2004 | Uchiyama |
| 2005/0043601 | A1 | 2/2005 | Kilcoyne et al. |
| 2005/0147559 | A1 | 7/2005 | von Alten |
| 2006/0021874 | A1 | 2/2006 | Hsiung et al. |
| 2006/0145876 | A1 | 7/2006 | Kimura et al. |
| 2006/0155174 | A1 | 7/2006 | Glukhovsky et al. |
| 2007/0138027 | A1 | 6/2007 | Dinsmoor et al. |
| 2007/0213659 | A1 | 9/2007 | Trovato et al. |
| 2008/0060952 | A1* | 3/2008 | Negron ................ 206/205 |

FOREIGN PATENT DOCUMENTS

| | | |
|---|---|---|
| DE | 3339323 | 5/1985 |
| JP | 2002532162 | 10/2002 |
| JP | 2003520108 | 7/2003 |
| JP | 2006509574 | 3/2006 |
| WO | WO03008637 | 1/2003 |
| WO | WO2005025647 | 3/2005 |
| WO | WO2005038049 | 4/2005 |
| WO | WO2006021932 | 3/2006 |
| WO | WO2006025013 | 3/2006 |
| WO | WO2006044049 | 4/2006 |
| WO | WO2006056944 | 6/2006 |
| WO | WO2006077529 | 7/2006 |
| WO | 2008030472 A2 | 3/2008 |
| WO | WO2008029372 | 3/2008 |
| WO | WO2008038199 | 4/2008 |
| WO | WO2008062335 | 5/2008 |

OTHER PUBLICATIONS

Translated Chinese Office Action mailed Nov. 4, 2013 for Chinese patent application No. 200980105514.0, a counterpart foreign application of U.S. Appl. No. 12/867,888, 13 pages.
Translated Chinese Office Action mailed Sep. 17, 2013 for Chinese patent application No. 200980112018.8, a counterpart foreign application of U.S. Appl. No. 12/933,891, 11 pages.
Translated Japanese Office Action mailed Sep. 24, 2013 for Japanese patent application No. 2011-501328, a counterpart foreign application of U.S. Appl. No. 12/933,891, 5 pages.
Translated Chinese Office Action mailed Jan. 15, 2013 for Chinese patent application No. 201080015953.5, a counterpart foreign application of U.S. Appl. No. 13/262,841, 17 pages.
Translated Chinese Office Action mailed Jan. 21, 2013 for Chinese patent application No. 201080040663.6, a counterpart foreign application of U.S. Appl. No. 13/390,111, 8 pages.
Translated Chinese Office Action mailed Mar. 14, 2013 for Chinese patent application No. 200980112018.8, a counterpart foreign application of U.S. Appl. No. 12/933,891, 12 pages.
Chinese Office Action mailed May 13, 2013 for Chinese patent application No. 201080015284.1, a counterpart foreign application of U.S. Appl. No. 13/262,861, 11 pages.
Evans, et al., "Measurement of Gastrointestinal pH Profiles in Normal Ambulant Human Subjects", GUT, vol. 29, 1988, pp. 1035-1041.
Translated Japanese Office Action mailed Apr. 16, 2013 for Japanese Patent Applicaiton No. 2011-514179, a counterpart foreign application of U.S. Appl. No. 12/992,305, 9 pages.
Translated Japanese Office Action mailed Apr. 30, 2013 for Japanese patent application No. 2010-546431, a counterpart foreign application of U.S. Appl. No. 12/867,888, 4 pages.
Kompella, et al., "Delivery System for Penetration Enhancement of Peptide and Protein Drugs: Design Considerations", Advanced Drug Delivery Reviews, vol. 46, 2001, pp. 211-245.
Paine, et al., "Characterization of Interintestinal and Intraintestinal Variations in Human CYP3A-Dependent Metabolism", The Journal of Pharmacology and Experimental Therapeutics, vol. 283, No. 3, 1997, pp. 1552-1562.
Siccardi, et al., "Regulation of Intestinal Epithelial Function: A Link Between Opportunities for Macromolecular Drug Delivery and Inflammatory Bowel Disease", Advanced Drug Delivery Reviews, vol. 57, 2005, pp. 219-235.

* cited by examiner

METHOD OF PREPARING A SWALLOWABLE CAPSULE COMPRISING A SENSOR

FIELD OF THE INVENTION

The present invention relates to method of preparing a swallowable capsule or pill comprising a sensor, e.g. a pH sensor or a sensor for particular ions or molecules, and to a kit of parts for carrying out such a method. The capsule can be swallowed by a patient and used for diagnostic purposes or for controllable release of a medicine.

BACKGROUND OF THE INVENTION

Electronically controlled ingestible capsules can be used to provide therapeutic or diagnostic treatment during traversal of the gastrointestinal alimentary tract. For example, an ingestible capsule can acquire diagnostic data as it traverses the gastrointestinal tract. If used for therapeutic treatment the capsule can be provided with an electronically controlled medicament delivery system. To that end it typically contains a battery, a medicine reservoir, a medicine dosing and delivering device, such as a pump, and electronic circuitry for controlling medicine delivery and optionally for two-way communication. The capsule moves through the intestines by the peristaltic movement of the muscles along the gastrointestinal tract.

The capsule comprises a sensor, e.g. a pH sensor for determining the location within the gastrointestinal tract. When the pill passes the pylorus, a pH step of about 3-4 is made. If the pill is used for controlled medication release this moment can be used as a trigger for controlled release in the small intestines. The drift velocity in the small intestines is dependent on the time of day. During or after a meal the intestines are more active than in between meals. Releasing medication directly after passage through the pylorus delivers the medication at the beginning of the jejunum releasing 2-3 hours later somewhere at the end of the jejunum and the beginning of the ileum releasing after 4-5 hours later it delivers the medication at the end of the ileum. As the value of the pH slowly increases from the beginning of the jejunum to halfway the small intestines the pH can also be used for triggering controlled release of medication. When passing through the ileocaecal valve (valvula Bauhini), the pH drops by 1-1.5 pH. This step can be used for triggering controlled release of medication at the beginning of the ascending colon. The motility of the large intestines is less dependent on mealtime and follows its own rhythm.

The pH value can for example be measured by using an electrochemical cell comprising an indicating electrode whose potential is directly proportional to the pH, a reference electrode whose potential is independent of the pH, and the liquid to be measured. The measured voltage is indicative for the pH of the liquid. The system is calibrated by placing the electrodes in solutions of known pH and measuring the corresponding voltages of the cell.

The electrodes are placed in a sample of the liquid to be measured. The voltage is then measured and the pH is determined using the calibration data.

The reference electrode used in pH measurements usually is a silver wire coated with silver chloride embedded by an electrolyte solution, e.g. of potassium chloride (KCl). The reference electrode must be in electrical contact with the pH electrode through the sample. Therefore the container with reference electrode and the electrolyte solution must communicate electrically with the sample, e.g., via a porous liquid junction, e.g., of ceramic, wood or plastic which allows ions to pass between the fill solution and the sample.

US 2004/0106849 discloses an electronic pill for diagnostic purposes comprising an ISFET type pH sensor.

Since the capsule must be swallowable, the capsule must be as small as possible. Therefore, there is only very limited space for the sensor and its components. However, the smaller the volume of electrolyte, the more it is susceptible of drying which limits the shelf life of the capsule.

SUMMARY OF THE INVENTION

The object of the invention is achieved with a kit comprising a swallowable capsule comprising a potentiometric sensor with an unfilled electrolyte cell wherein the kit further comprises a separate container containing a liquid electrolyte. This way, the electrolyte cell in the capsule can be filled only shortly before use. The shelf life of the capsule is not limited anymore by the drying of the electrolyte and the electrolyte cell can be made even smaller.

Optionally, the kit further comprises one or more containers comprising buffer liquids for calibration. This allows calibration of the sensor just after filling the electrolyte cell and after activation of the capsule.

The capsule, the electrolyte container, and optionally the buffer liquid containers can be separately packed, e.g., in a single blister packing, optionally having a breaking line between the part packing the capsule and the rest of the packed parts.

The invention also relates to a method of preparing an electronic capsule with a potentiometric sensor comprising control circuitry and an electrolyte cell wherein the electrolyte cell is provided with one or more openings, wherein the cell is first filled via one or more of the openings with an electrolyte. The capsule can for instance be provided with a septum, allowing filling of the electrolyte cell by means of a syringe of corresponding dimensions.

After filling the electrolyte cell a start-up station can be used to activate the capsule. An automatic calibration procedure can be initiated and optionally the capsule can be programmed to controllably release a medicament at areas where the measured pH is within a pre-determined range.

After filling, the capsule can be calibrated by contacting the electrolyte in the electrolyte cell with a buffer liquid. The calibration can take place in more than one step, using different buffer liquids.

A start-up station can be used which comprises at least two openings for receiving the capsule, wherein at least one of the openings is within the scope of electro-inductive control circuitry for activating the capsule and at least one of the openings is a hole filled with the liquid electrolyte, the hole being dimensioned to receive the capsule leaving one or more venting openings free.

In a particular embodiment the electrolyte filled hole in the start-up station can form the piston chamber of a piston opposite the open end of the hole, the open end being provided with a sealing ring.

The start-up station can comprise one or more further holes at least partly filled with respective buffer liquids.

The sensor can for example be based on ISFET (ion sensitive field effect transistor) technology. An ISFET is a transistor with an electrical source-drain connection with the area of the gate in contact with the fluid to be measured. If the ISFET is used as a pH sensor, the surface of the source drain area is covered with an H+ sensitive coating. If the ISFET is used as a sensor for another type of ion or molecule, the source drain area is coated with a layer that is specifically sensitive for these particular ions or molecules.

The reference electrode can for instance be a silver wire or platelet coated with silver chloride.

In order to contact the electrolyte with the direct environment, the electrolyte cell can be provided with one or more openings or one or more frit windows, e.g. of a porous ceramic and/or polymeric material.

The electrolyte can for instance be a saturated potassium chloride gel or solution, e.g., a potassium chloride solution in water with a thickener, such as starch. The composition can be made biologically inactive by adding a sterilizing agent.

The capsule can be part of a system comprising a start-up station, to calibrate the sensors and program the release profile of the medication as a function of time, place and/or sensory input.

The capsule can be provided with a transceiver, e.g. a transceiver that operates in the MICS band (402-405 MHz), the 433 HHz band or even at a much lower frequency (e.g. several 100 KHz) and has a reach of at most a few meters. The capsule can be arranged to communicate with a portable device arranged to communicate with a base station that is located near the patient with e.g. an infrared link, WiFi, Bluetooth, Zigbee. Such a base station can be a PDA, for instance. Optionally, the base station or the portable unit communicates with the doctor, the pharmacy, the caregiver or a researcher, e.g., via the Internet.

Besides the pH sensor, the capsule can also be provided with a temperature sensor, such as a digital temperature sensitive IC and/or a MEMS (miniature electro-chemical system) pressure transducer. Optionally, the capsule can comprise other types of sensors, e.g., biosensors.

The capsule can be used for medicinal or veterinary purposes. For human patients the capsule will preferably be pill-shaped and not be larger than about 2-3 cm with a diameter of about 1 cm or less.

BRIEF DESCRIPTION OF THE DRAWINGS

The present invention will be elucidated with reference to the figures wherein.

DETAILED DESCRIPTION OF EMBODIMENTS

Figure 1:
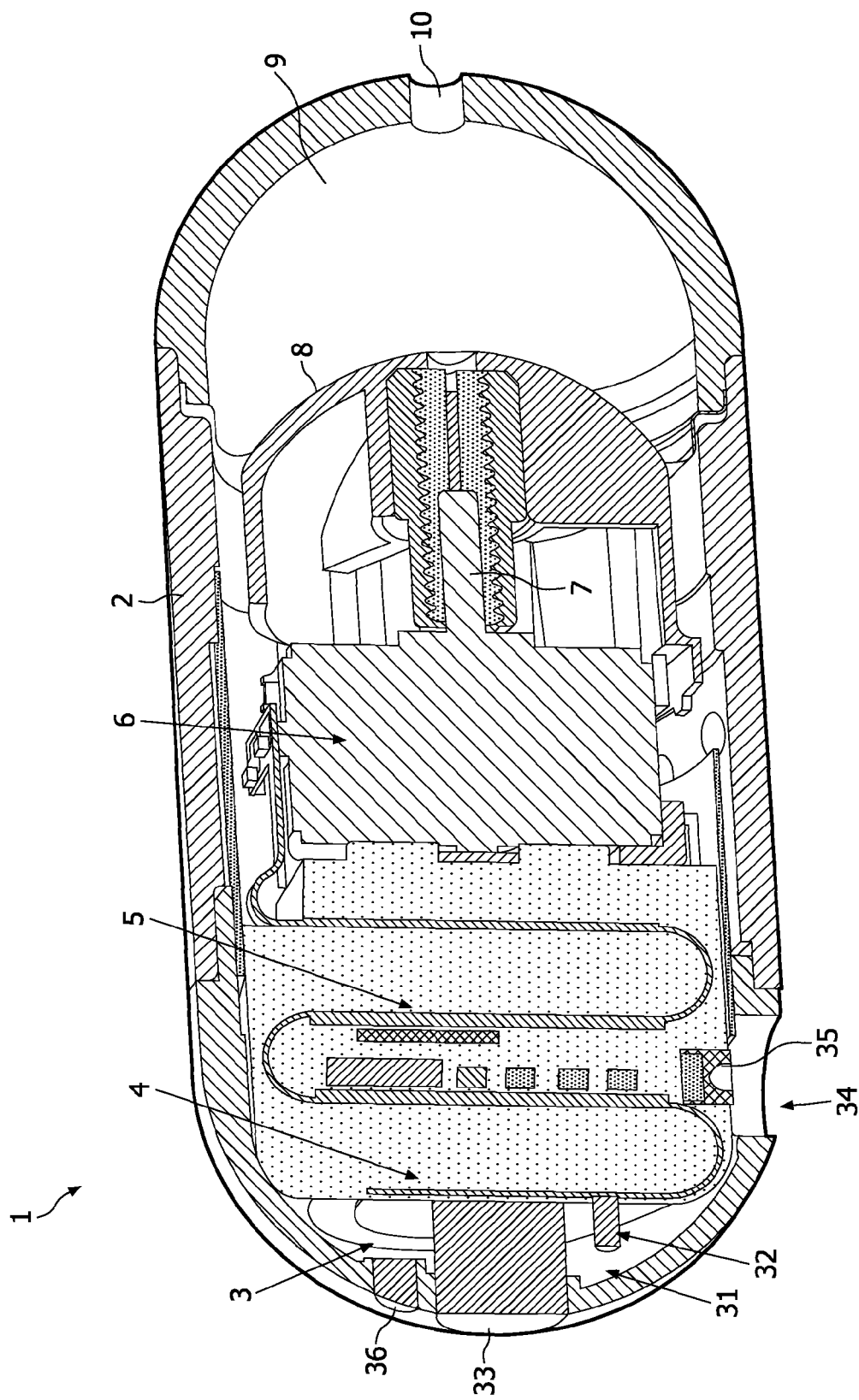
FIG. 1 shows in perspective cross section a capsule for use in a kit and a method according to the present invention.

FIG. 1 shows in perspective a cross section of an electronic pill 1 with a housing 2 encasing a sensor assembly 3, a battery 4, electronic circuitry 5, including transceiver circuitry, start-up circuitry and an antenna, a stepper motor 6 for powering a driving mechanism 7 which drives a piston 8 for dosing medicament present in a medicament reservoir 9, which can be dispensed via dispensing hole 10.

The sensor assembly 3 comprises a cell 31 for containing an electrolyte gel. Located in the electrolyte cell 31 is a reference electrode 32. Electrolyte in the cell 32 is in contact with the environment via a frit window 33 of a porous ceramic, glass or polymeric material. Via an opening 34 in the housing 2, an ISFET 35 is in contact with the environment with its source drain surface. The housing 2 is provided with a septum 36 for filling the electrolyte cell 31, e.g., by means of a syringe. Overflow and venting openings (not shown) can be provided in the housing adjacent the electrolyte cell to allow easy filling of the cell 31.

Figure 2:
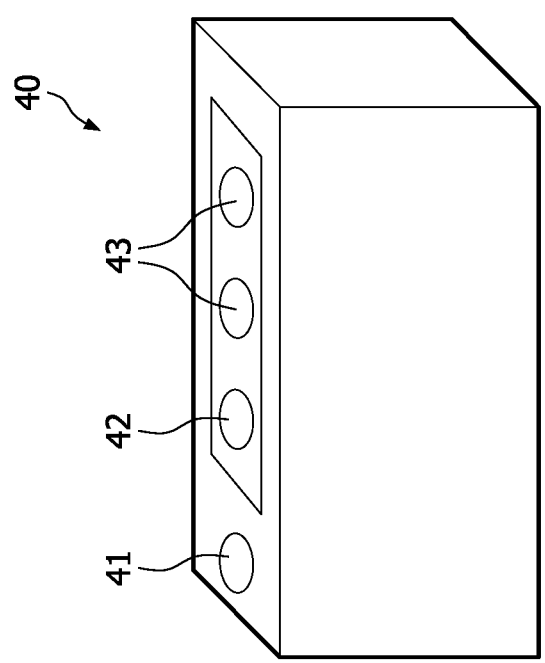
FIG. 2 shows schematically a start-up station for use in a method according to the present invention.
Figure 3:
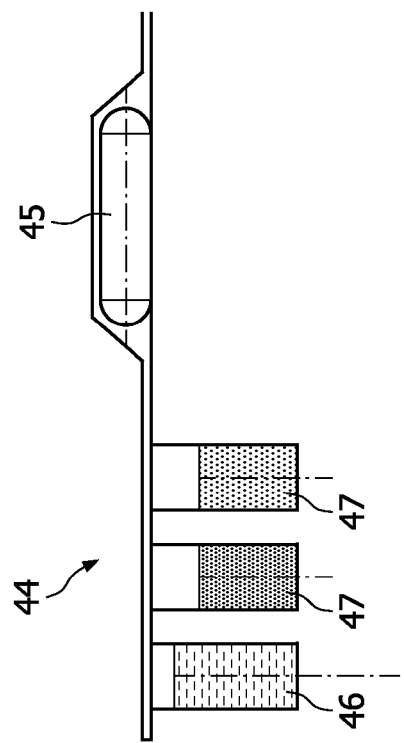
FIG. 3 shows a blister packing a pill for use with the start-up station of FIG. 2.
Figure 4:
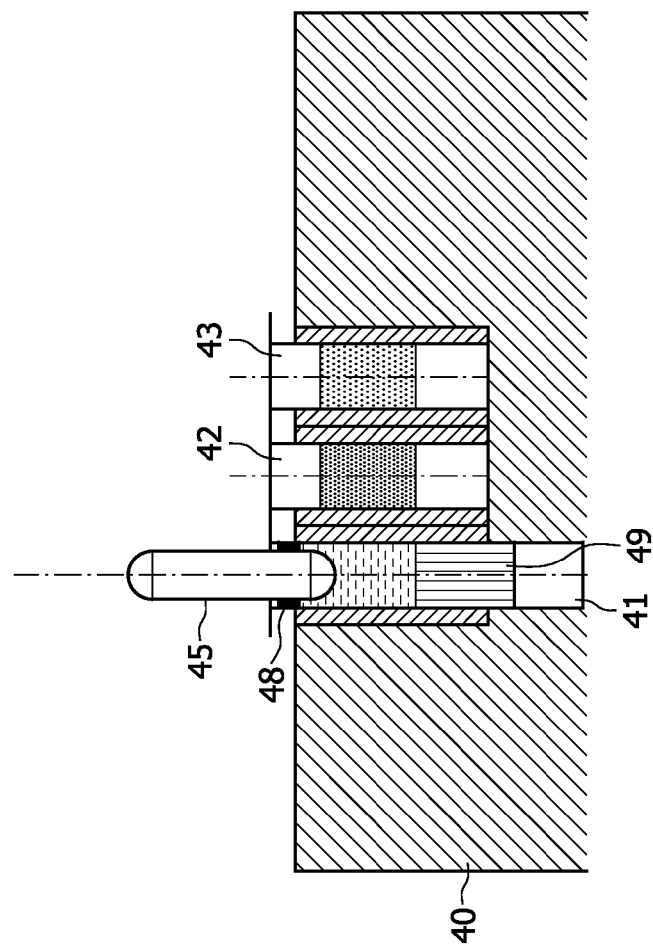
FIG. 4 shows a cross section of the start-up station of FIG. 2 in use.

A particular embodiment of a system for preparing an electronic pill is shown in FIGS. 2, 3 and 4. FIG. 2 shows a start-up station 40 having a start-up opening or hole 41 for receiving an electronic pill, an opening 42 for receiving an electrolyte container, and calibration openings or holes 43 for receiving containers with pH buffer liquids.

FIG. 3 shows schematically a blister packaging 44 packing an electronic pill 45, a container 46 for an electrolyte gel, and two containers 47 containing pH buffers. The blister 44 has a breaking line allowing the pill 45 to be handled separately from the containers 46, 47. After unpacking the pill 45, it is inserted in the start-up opening 41. This opening 41 is partly surrounded by electronic start-up circuitry, such as a start-up coil. The electrolyte container 46 and the pH buffer containers 47 are also unpacked and inserted in the openings 42 and 43 respectively, as shown in FIG. 4 showing the start-up station 40 in cross section. The container 46 comprising the electrolyte gel is provided with a sealing ring 48 along the edge of its open side. The ring 48 serves to seal against the electronic pill 45 when it is inserted in the container 47, to prevent leakage of electrolyte gel. The bottom of the opening 42 for the electrolyte container 46 is formed by a piston 49 to press the electrolyte container upwards, forcing the electrolyte gel to enter the electrolyte cell of the pill 45 via one or more openings, which are optionally provided with a no-return valve. The pill is provided with venting openings (not shown) located in such a way that these are not immersed in the electrolyte gel when the pill 45 is inserted in the container 46.

After filling the electrolyte cell of the pill 45, the pH sensor of the pill 45 is inserted in the pH buffer liquids for calibration. After calibration, the pill deactivates itself automatically. The pill 45 is ready for use and can be programmed with a prescribed dispensing profile. If the pill 45 is to be used at a later moment, the openings in the electrolyte cell of the pill 45 can temporarily be covered to avoid evaporation of the electrolyte gel, e.g., with a sticker or a paste which easily dissolves in the stomach environment.

Figure 5:
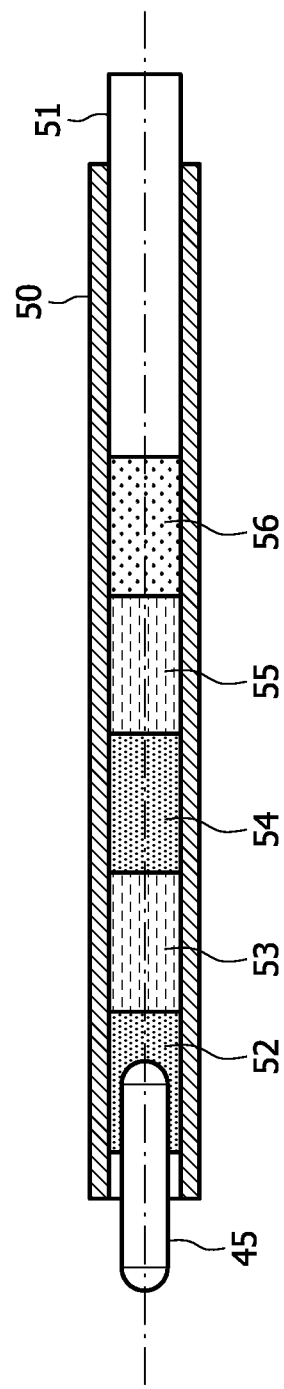
FIG. 5 shows in cross section device for preparing a capsule with a method according to the present invention.

FIG. 5 shows a syringe 50 forming a microfluidic system. The syringe 50 comprises a piston 51, which can be hand-driven and a series of separate compartments. Starting from the end of the syringe opposite the end receiving the piston, the compartments include a first compartment 52 containing an electrolyte gel, a second compartment 53 containing a flushing fluid, a third compartment 54 containing a pH buffer, a fourth compartment 55 containing a flushing fluid, and a fifth compartment 56 containing a second pH buffer having a pH different from the pH of the first pH buffer. The compartments 52-56 are separated by thin membranes and can be pushed forward by means of the piston 51. To prepare a pill for use, the syringe 50 is placed in a slot of a start-up station. The end of the syringe 50 is closed off by a seal 57 which is broken by inserting a pill 45. The electrolyte gel in the first compartment 52 is pressed into the electrolyte cell of the pill 45. Subsequently, the pill 45 is activated by the start-up station, receiving commands to perform a calibration autonomously. The syringe 50 presses the second compartment 53 onto the pill 45 until the membrane breaks and the pill is flushed by the flushing fluid. Moving the piston 51 further, the pill 45 is contacted with the first pH buffer and the first calibration is carried out. When the piston 51 is moved further, the membrane of the second flushing fluid compartment 55 breaks and the pill 45 is flushed again. Finally, the piston 51 pushes the final compartment 56 with the second pH buffer over the pill 45 and the second calibration is carried out.

Optionally, the piston 51 of the syringe 50 can be driven by a tool, such as a screw rod driven by a controllable electrical motor. That way, the filling step and the calibration steps can be carried out automatically.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

The invention claimed is:

1. A kit comprising:
   a capsule comprising a potentiometric sensor with an unfilled electrolyte cell;
   a liquid electrolyte container containing a liquid electrolyte; and
   one or more buffer liquid containers containing buffer liquids for calibration, wherein the capsule, the liquid electrolyte container and the buffer liquid containers are contained in separated portions of a single package configured to be received in at least one opening of a start-up station.

2. The kit according to claim 1 wherein the potentiometric sensor is a pH sensor.

3. The kit according to claim 1 wherein the capsule and the electrolyte container are separately packed in a single blister packing.

4. A method of preparing a swallowable capsule comprising a potentiometric sensor having an electrolyte cell, the method comprising:
   providing a single packing comprising, the swallowable capsule, a liquid electrolyte container containing a liquid electrolyte, and a buffer liquid container containing a buffer liquid, wherein the swallowable capsule, the liquid electrolyte container, and the buffer liquid container are separated within the single packing;
   placing at least a portion of the single packing in an opening of a startup station; and
   in response to placing the at least the portion of the single packing in the opening of the startup station, with the single packing being retained in the startup station, causing the liquid electrolyte to fill the electrolyte cell.

5. The method according to claim 4 further comprising activating the capsule with the startup station after filling the electrolyte cell.

6. The method according to claim 5 further comprising calibrating the capsule by contacting the electrolyte in the electrolyte cell with a buffer liquid.

7. The method Method according to claim 6 wherein the calibrating is repeated for one or more additional buffer liquids.

8. A start-up station for use in a method according to claim 4 wherein the start-up station comprises at least two openings for receiving a capsule, wherein at least one of the openings is within the scope of electro-inductive control circuitry for activating the capsule and at least one of the openings is an opening for containing the liquid electrolyte, the opening being dimensioned to receive the capsule leaving one or more venting openings free.

9. The start-up station according to claim 8 wherein the electrolyte filled opening forms the piston chamber of a piston opposite the open end of the opening, the open end being provided with a sealing ring.

10. The start-up station according to claim 9 wherein the station comprises one or more further openings at least partly filled with respective buffer liquids.

* * * * *